US009695274B2

(12) United States Patent
Hayer et al.

(10) Patent No.: US 9,695,274 B2
(45) Date of Patent: Jul. 4, 2017

(54) POLYMERS CONTAINING 2,7-PYRENE STRUCTURAL UNITS

(71) Applicant: Merck Patent GmbH, Darmstadt (DE)

(72) Inventors: Anna Hayer, Mainz (DE); Niels Schulte, Kelkheim (DE)

(73) Assignee: Merck Patent GmbH (DE)

( * ) Notice: Subject to any disclaimer, the term of this patent is extended or adjusted under 35 U.S.C. 154(b) by 207 days.

(21) Appl. No.: 14/409,508

(22) PCT Filed: Jun. 12, 2013

(86) PCT No.: PCT/EP2013/001722
§ 371 (c)(1),
(2) Date: Dec. 19, 2014

(87) PCT Pub. No.: WO2014/000860
PCT Pub. Date: Jan. 3, 2014

(65) Prior Publication Data
US 2015/0322198 A1    Nov. 12, 2015

(30) Foreign Application Priority Data
Jun. 29, 2012  (EP) ..................................... 12004858

(51) Int. Cl.
| H01B 1/00 | (2006.01) |
| C08G 61/10 | (2006.01) |
| C08L 65/02 | (2006.01) |
| C07F 5/04 | (2006.01) |
| C08G 61/12 | (2006.01) |
| H01L 51/00 | (2006.01) |
| H01B 1/12 | (2006.01) |
| C09K 11/06 | (2006.01) |
| H05B 33/14 | (2006.01) |
| H01L 51/50 | (2006.01) |

(52) U.S. Cl.
CPC .............. *C08G 61/10* (2013.01); *C07F 5/04* (2013.01); *C08G 61/12* (2013.01); *C08G 61/128* (2013.01); *C08L 65/02* (2013.01); *C09K 11/06* (2013.01); *H01B 1/124* (2013.01); *H01L 51/0036* (2013.01); *H01L 51/0039* (2013.01); *H01L 51/0043* (2013.01); *H05B 33/14* (2013.01); *C08G 2261/12* (2013.01); *C08G 2261/1412* (2013.01); *C08G 2261/312* (2013.01); *C08G 2261/314* (2013.01); *C08G 2261/3142* (2013.01); *C08G 2261/3162* (2013.01); *C08G 2261/411* (2013.01); *C08G 2261/5222* (2013.01); *C08G 2261/95* (2013.01); *C08L 2203/20* (2013.01); *C09K 2211/1416* (2013.01); *H01L 51/5012* (2013.01); *Y02E 10/549* (2013.01)

(58) Field of Classification Search
CPC ............. H01L 51/0043; H01L 51/0036; H01L 51/0039; H01L 51/5012; C07F 5/04; C08G 2261/12; C08G 2261/1412; C08G 2261/312; C08G 2261/314; C08G 2261/3142; C08G 2261/3162; C08G 2261/411; C08G 2261/5222; C08G 2261/95; C08G 61/10; C08G 61/12; C08G 61/128; C08L 2203/20; C08L 65/02; C09K 11/06; C09K 2211/1416; H05B 33/14; Y02E 10/549; H01B 1/124
See application file for complete search history.

(56) References Cited

U.S. PATENT DOCUMENTS

| 2009/0179196 | A1 | 7/2009 | Adachi et al. | |
| 2011/0278560 | A1* | 11/2011 | Zhou | C08G 61/02 257/40 |
| 2012/0305082 | A1* | 12/2012 | Moon | C08G 61/126 136/263 |
| 2014/0183469 | A1* | 7/2014 | Jakobsson | H01L 51/56 257/40 |

FOREIGN PATENT DOCUMENTS

| CN | 1785943 A | 6/2006 |
| DE | 102008052314 A1 | 4/2010 |
| EP | 0964045 A1 | 12/1999 |
| WO | WO-2010006852 A1 | 1/2010 |
| WO | WO-2010087840 A1 | 8/2010 |
| WO | WO-2010136353 A1 | 12/2010 |
| WO | WO-2011127301 A2 | 10/2011 |
| WO | WO-2011138935 A1 | 11/2011 |

(Continued)

OTHER PUBLICATIONS

Li, X.G. et al., "Simple Efficient Synthesis of Strongly Luminescent Polypyrene with Intrinsic Conductivity and High Carbon Yield by Chemical Oxidative Polymerization of Pyrene," Chem. Eur. J. 2010, 16, 4803-4813.*
Coventry, D., et al., "Selective Ir-catalysed borylation of polycyclic aromatic hydrocarbons: structures of naphthalene-2,6-bis(boronate), pyrene-2,7-bis(boronate) and perylene-2,5,8,11-tetra(boronate) esters", Chemical Communications, (2005), pp. 2172-2174.
Crawford, A., et al., "Synthesis of 2- and 2,7-Functionalized Pyrene Derivatives: An Application of Selective C-H Borylation", Chemistry A European Journal, vol. 18, (2012), pp. 5022-5035.
International Search Report for PCT/EP2013/001722 mailed Aug. 9, 2013.

(Continued)

*Primary Examiner* — Mark Kopec
*Assistant Examiner* — Jaison Thomas
(74) *Attorney, Agent, or Firm* — Drinker Biddle & Reath LLP

(57) ABSTRACT

The present invention relates to polymers containing 2,7-pyrene structural units, to a process for the preparation thereof, and to blends and formulations comprising these polymers. The present invention furthermore relates to the use of the polymers or blends according to the invention in electronic devices and to electronic devices, in particular OLEDs, comprising the polymers or blends according to the invention.

15 Claims, No Drawings

(56) References Cited

FOREIGN PATENT DOCUMENTS

| WO | WO 2011/150573 | * 12/2011 | ......... C08G 2261/12 |
| WO | WO-2012037090 A2 | 3/2012 | |

OTHER PUBLICATIONS

Kawano, S., et al., "Blue-Emitting Poly(2,7-pyrenylene)s: Synthesis and Optical Properties", Macromolecules, vol. 41, (2008), pp. 7933-7937.

Lee, H., et al., "Synthesis of 2,7-Dibromopyrene", Journal of Organic Chemistry, vol. 51, No. 14, (1986), pp. 2847-2848.

Wan, S., et al., "A Belt-Shaped, Blue Luminescent, and Semiconducting Covalent Organic Framework", Angewandte Chemie International Edition, vol. 47, (2008), pp. 8826-8830.

Wan, S., et al., "A Photoconductive Covalent Organic Framework: Self-Condensed Arene Cubes Composed of Eclipsed 2D Polypyrene Shets for Photocurrent Generation", Angewandte Chemie International Edition, vol. 48, (2009), pp. 5439-5442.

Cheng, Y-J, et al., "Synthesis of Conjugated Polymers for Organic Solar Cell Applications", Chem. Rev., 2009, vol. 109, pp. 5868-5923.

Grimsdale, A., et al., "Synthesis of Light-Emitting Conjugated Polymers for Applications in Electroluminescent Devices", Chem. Rev., 2009, vol. 109, pp. 897-1091.

Kiebooms, R., et al., "Synthesis, Electrical, and Optical Properties of Conjugated Polymers", Handbook of Advanced Electronic and Photonic Materials and Devices, Bd. 8, 2001, XP001029240, pp. 1-102.

Vollmann, H., et al., "Pyrene and its derivatives", Justus Liebigs Annalen Der Chemie, 1937, Bd. 531, Nr. 1, XP008163965, pp. 1-159.

European Office action mailed Oct. 4, 2016 for EP 13728120.0.

\* cited by examiner

POLYMERS CONTAINING 2,7-PYRENE STRUCTURAL UNITS

CROSS-REFERENCE TO RELATED APPLICATIONS

This application is a national stage application (under 35 U.S.C. §371) of PCT/EP2013/001722, filed Jun. 12, 2013, which claims benefit of European Application No. 12004858.2, filed Jun. 29, 2012, both of which are incorporated herein by reference in their entirety.

The present invention relates to polymers containing 2,7-pyrene structural units, to a process for the preparation thereof and to blends and formulations comprising these polymers. The present invention furthermore relates to the use of the polymers or blends according to the invention in electronic devices and to electronic devices, in particular OLEDs, comprising the polymers or blends according to the invention.

Compounds such as the polymers according to the invention are being developed for a number of different applications which can be ascribed in the broadest sense to the electronics industry. The structure of organic electroluminescent devices (OLEDs) in which these organic semiconductors are preferably employed, inter alia, as functional materials is described, for example, in U.S. Pat. No. 4,539,507, U.S. Pat. No. 5,151,629, EP 0676461 and WO 98/27136.

The prior art discloses various polymeric materials which are suitable for use in organic electroluminescent devices. Thus, for example, compounds based on monomer units such as spirobifluorene, fluorene, indenofluorene, phenanthrene or dihydrophenanthrene are disclosed in WO 04/041901, WO 04/113412 and WO 05/014689.

However, there continues to be a demand for novel materials for use in organic electronic devices, in particular with regard to an improvement of the devices in the following respects:

1. Materials having a larger band gap are required, so that deeper-blue singlet emission can be achieved for display applications having a large colour space. Larger band gaps in polymers would additionally enable these to be used as host materials not only for red, but also for green triplet emission.
2. The lifetime and efficiency of organic electroluminescent devices should be increased further, in particular in the case of blue-emitting systems and with respect to high-value applications.

The present invention is thus based on the object of providing novel materials for electronic devices which have a larger band gap and improve the lifetime and efficiency of organic electroluminescent devices.

Surprisingly, it has been found that compounds containing 2,7-pyrene units can successfully be employed as materials in electronic devices, preferably organic electroluminescent devices.

The present application thus relates to a polymer containing one or more structural units of the following formula (I),

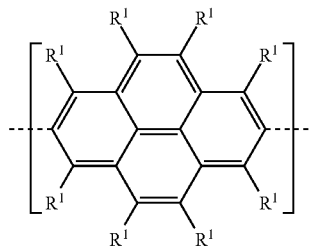

where
$R^1$ on each occurrence, identically or differently, H, D, F, Cl, Br, I, OH, $N(R^2)_2$, a straight-chain alkyl, alkoxy or thioalkoxy group having 1 to 40 C atoms or a branched or cyclic alkyl, alkoxy or thioalkoxy group having 3 to 40 C atoms, in which, in addition, one or more H atoms may be replaced by $R^2$ and in which, in addition, one or more non-adjacent $CH_2$ groups may be replaced by O, S, $Si(R^2)_2$, $Ge(R^2)_2$, $BR^2$, $NR^2$, $PR^2$, CO, C=S, C=Se, C=$NR^2$, $PO(R^2)$, $PS(R^2)$, $R^2C$=$CR^2$, C≡C, SO, $SO_2$, COO, O(CO)O or $CONR^2$, or a mono- or polycyclic, aromatic or heteroaromatic ring system;
$R^2$ on each occurrence, identically or differently, H, F, a straight-chain alkyl, alkoxy or thioalkoxy group having 1 to 40 C atoms or a branched or cyclic alkyl, alkoxy or thioalkoxy group having 3 to 40 C atoms, in which, in addition, one or more H atoms may be replaced by F and in which, in addition, one or more non-adjacent $CH_2$ groups may be replaced by O, CO, COO or O(CO)O, or a mono- or polycyclic, aromatic or heteroaromatic ring system; and
the dashed lines represent the bonds to the adjacent structural units in the polymer.

The polymers according to the invention preferably contain 2 to 10,000 recurring units, where the term "polymer" in the present application is intended to encompass both polymers and also dendrimers and oligomers. The oligomeric compounds according to the invention have 2 to 9 recurring units. Preferred polymers and dendrimers according to the invention contain in total 10 to 10,000 recurring units. The degree of branching DB of the polymers and dendrimers here can be between 0 (linear polymer without branching points) and 1 (fully branched dendrimer).

The polymers according to the invention preferably have a molecular weight $M_w$ in the range from 1,000 to 2,000,000 g/mol, particularly preferably a molecular weight $M_w$ in the range from 10,000 to 1,500,000 g/mol and very particularly preferably a molecular weight $M_w$ in the range from 50,000 to 1,000,000 g/mol. The molecular weight $M_w$ is determined by means of GPC(=gel permeation chromatography) against an internal polystyrene standard.

In the embodiment according to the invention, the proportion of the structural units of the formula (I) in the polymer is 0.01 to 100 mol %, preferably 1 to 95 mol %, particularly preferably 10 to 80 mol % and very particularly preferably 30 to 60 mol %.

The term "mono- or polycyclic, aromatic ring system" in the present application is taken to mean an aromatic ring system having 6 to 60, preferably 6 to 30, particularly preferably 6 to 14 and very particularly preferably 6 to 10 aromatic ring atoms, which does not necessarily contain only aromatic groups, but instead in which a plurality of aromatic units may also be interrupted by a short non-aromatic unit (<10% of the atoms other than H, preferably <5% of the atoms other than H), such as, for example, sp³-hybridised C atom or O or N atom, CO group, etc. Thus, for example, systems such as 9,9'-spirobifluorene, 9,9-diarylfluorene, etc., are also intended to be taken to be aromatic ring systems.

The aromatic ring systems may be mono- or polycyclic, i.e. they may have one ring (for example phenyl) or a plurality of rings, which may also be condensed (for example naphthyl) or covalently linked (for example biphenyl), or contain a combination of condensed and linked rings.

Preferred aromatic ring systems are, for example, phenyl, biphenyl, terphenyl, naphthyl, binaphthyl, phenanthrene, dihydrophenanthrene, pyrene, dihydropyrene, chrysene, fluorene, indene, indenofluorene and spirobifluorene.

The term "mono- or polycyclic, heteroaromatic ring system" in the present application is taken to mean an aromatic ring system having 5 to 60, preferably 5 to 30, particularly preferably 5 to 20 and very particularly preferably 5 to 9 aromatic ring atoms, where one or more of these atoms is (are) a heteroatom.

The "mono- or polycyclic, heteroaromatic ring system" does not necessarily contain only aromatic groups, but instead may also be interrupted by a short non-aromatic unit (<10% of the atoms other than H, preferably <5% of the atoms other than H), such as, for example, sp³-hybridised C atom or O or N atom, CO group, etc.

The heteroaromatic ring systems may be mono- or polycyclic, i.e. they may have one ring or a plurality of rings, which may also be condensed or covalently linked (for example pyridylphenyl), or contain a combination of condensed and linked rings. Preference is given to fully conjugated heteroaryl groups.

Preferred heteroaromatic ring systems are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno-[3,2b]thiophene, dithienothiophene, isobenzothiophene, dibenzothiophene, benzothiadiazothiophene or combinations of these groups.

The mono- or polycyclic, aromatic or heteroaromatic ring system may be unsubstituted or substituted. Substituted in the present application means that the mono- or polycyclic, aromatic or heteroaromatic ring system has one or more substituents $R^1$.

Preferred structural units of the formula (I) are represented by the formulae (Ia) to (Ic) shown below, where the formula (Ic) is particularly preferred.

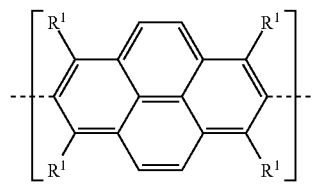
(Ia)

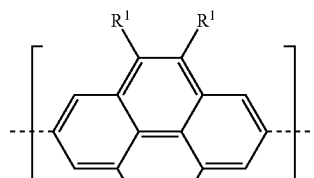
(Ib)

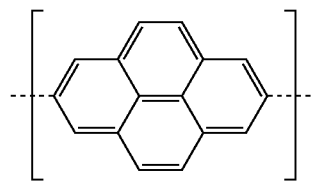
(Ic)

The dashed lines in the formulae (Ia), (Ib) and (Ic) here represent the bonds to the adjacent structural units in the polymer. $R^1$ in the formulae (Ia) and (Ib) here can adopt the meanings indicated for $R^1$ in relation to formula (I).

$R^1$ in the formulae (I), (Ia) and (Ib) is preferably on each occurrence, identically or differently, a straight-chain alkyl or alkoxy group having 1 to 10 C atoms, particularly preferably having 1 to 6 C atoms, or a branched alkyl or alkoxy group having 3 to 10 C atoms, particularly preferably having 3 to 6 C atoms, an aromatic ring system having 6 to 30, particularly preferably having 6 to 18 aromatic ring atoms or a heteroaromatic ring system having 5 to 30, particularly preferably having 5 to 20 ring atoms, of which at least one ring atom is a heteroatom. The aromatic or heteroaromatic ring system here may either be unsubstituted or substituted by one or more radicals $R^3$, where $R^3$ is, identically or differently, a straight-chain alkyl or alkoxy group having 1 to 10 C atoms, particularly preferably having 1 to 6 C atoms, or a branched alkyl or alkoxy group having 3 to 10 C atoms, particularly preferably having 3 to 6 C atoms.

In a preferred embodiment of the present invention, the polymer according to the invention, besides one or more structural units of the formula (I), also contains at least one further structural unit which is different from the structural unit of the formula (I). These are, inter alia, those as disclosed and extensively listed in WO 02/077060 A1 and in WO 2005/014689 A2. These are regarded as part of the present application by way of reference. The further structural units can originate, for example, from the following classes:

group 1: units which influence the hole-injection and/or hole-transport properties of the polymers;

group 2: units which influence the electron-injection and/or electron-transport properties of the polymers;

group 3: units which have combinations of individual units of group 1 and group 2;

group 4: units which modify the emission characteristics to such an extent that electrophosphorescence can be obtained instead of electrofluorescence;

group 5: units which improve transfer from the singlet state to the triplet state;

group 6: units which influence the emission colour of the resultant polymers;

group 7: units which are typically used as polymer backbone;

group 8: units which influence the film morphology and/or the rheology of the resultant polymers.

Structural units from group 1 which have hole-injection and/or hole-transport properties are, for example, triarylamine, benzidine, tetraaryl-para-phenylenediamine, triarylphosphine, phenothiazine, phenoxazine, dihydrophenazine, thianthrene, dibenzo-para-dioxin, phenoxathiyne, carbazole, azulene, thiophene, pyrrole and furan derivatives and further O—, S— or N— containing heterocycles having a high HOMO (HOMO=highest occupied molecular orbital). These arylamines and heterocycles preferably result in an HOMO in the polymer of greater than −5.8 eV (against vacuum level), particularly preferably greater than −5.5 eV.

Structural units from group 2 which have electron-injection and/or electron-transport properties are, for example, pyridine, pyrimidine, pyridazine, pyrazine, oxadiazole, quinoline, quinoxaline, anthracene, benzanthracene, pyrene, benzimidazole, triazine, ketone, phosphine oxide and phenazine derivatives, but also triarylboranes and further O—, S— or N— containing heterocycles having a low LUMO (LUMO=lowest unoccupied molecular orbital). These units in the polymer preferably result in an LUMO of less than −1.5 eV (against vacuum level), particularly preferably less than −2.0 eV.

It may be preferred for the polymers according to the invention to contain units from group 3 in which structures which influence the hole mobility and structures which influence the electron mobility (i.e. units from group 1 and 2) are bonded directly to one another or to contain structures which influence both the hole mobility and the electron mobility. Some of these units can serve as emitters and shift the emission colour into the green, yellow or red. Their use is thus suitable, for example, for the generation of other emission colours from originally blue-emitting polymers.

Structural units from group 4, so-called triplet emitter units, are those which are able to emit light from the triplet state with high efficiency, even at room temperature, i.e. exhibit electrophosphorescence instead of electrofluorescence, which frequently causes an increase in the energy efficiency. A triplet emitter unit in the present application is taken to mean a compound which includes a triplet emitter. Triplet emitters in the present application are taken to mean all compounds which are capable of emitting light in the visible or NIR region through transfer from a triplet state into an energetically lower state. This is also referred to as phosphorescence. Suitable for this purpose are firstly compounds which contain heavy atoms having an atomic number of greater than 36. Preference is given to compounds which contain d- or f-transition metals which satisfy the above-mentioned condition. Particular preference is given here to corresponding structural units which contain elements of group 8 to 10 of the Periodic Table (Ru, Os, Rh, Ir, Pd, Pt). Suitable structural units for the polymers according to the invention here are, for example, various complexes, as described, for example, in WO 02/068435 A1, in WO 02/081488 A1 and in EP 1239526 A2. Corresponding monomers are described in WO 02/068435 A1 and in WO 2005/042548 A1. It is preferred in accordance with the invention to employ triplet emitters which emit in the visible spectral region (red, green or blue). The triplet emitter may be part of the backbone of the polymer (i.e. in the main chain of the polymer) or it may be located in a side chain of the polymer.

Structural units from group 5 are those which improve transfer from the singlet state to the triplet state and which, employed in support of the above-mentioned triplet emitter units, improve the phosphorescence properties of these structural elements. Suitable for this purpose are, in particular, carbazole and bridged carbazole dimer units, as described, for example, in WO 2004/070772 A2 and in WO 2004/113468 A1. Also suitable for this purpose are ketones, phosphine oxides, sulfoxides, sulfones, silane derivatives and similar compounds, as described, for example, in WO 2005/040302 A1.

Structural units from group 6, besides those mentioned above, are those which have at least one further aromatic structure or another conjugated structure which do not fall under the above-mentioned groups, i.e. which have only little influence on the charge-carrier mobilities, are not organometallic complexes or do not influence singlet-triplet transfer. Structural elements of this type can influence the emission colour of the resultant polymers. Depending on the unit, they can therefore also be employed as emitters. Preference is given here to aromatic structures having 6 to 40 C atoms or also tolan, stilbene or bisstyrylarylene derivatives, each of which may be substituted by one or more radicals $R^1$. Particular preference is given here to the incorporation of 1,4 phenylene, 1,4-naphthylene, 1,4- or 9,10-anthrylene, 1,6-, 2,7- or 4,9-pyrenylene, 4,4'-biphenylylene, 4,4" terphenylylene, 4,4'-bi-1,1-naphthylylene, 4,4'-tolanylene, 4,4'-stilbenylene, 4,4" bisstyrylarylene, benzothiadiazole and corresponding oxygen derivatives, quinoxaline, phenothiazine, phenoxazine, dihydrophenazine, bis(thiophenyl)arylene, oligo(thiophenylene), phenazine, rubrene, pentacene or perylene derivatives, which are preferably substituted, or preferably conjugated push-pull systems (systems which are substituted by donor and acceptor substituents) or systems such as squarines or quinacridones, which are preferably substituted.

Structural units from group 7 are units which have aromatic structures having 6 to 40 C atoms, which are typically used as polymer backbone. These are preferably 4,5-dihydropyrene derivatives, 4,5,9,10-tetrahydropyrene derivatives, fluorene derivatives, 9,9'-spirobifluorene derivatives, phenanthrene derivatives, 9,10-dihydrophenanthrene derivatives, 5,7-dihydrodibenzoxepine derivatives and cis- and trans-indenofluorene derivatives, but in principle also all similar structures which, after polymerisation, would result in a conjugated, bridged or unbridged polyphenylene or polyphenylene-vinylene homopolymer. Here too, the said aromatic structure may contain heteroatoms, such as O, S or N, in the backbone or a side chain.

Structural units from group 8 are those which influence the film morphology and/or the rheology of the polymers, such as, for example, siloxanes, long alkyl chains or fluorinated groups, but also particularly rigid or flexible units, such as, for example, liquid crystal-forming units or cross-linkable groups. Preferred polymers according to the invention are those in which at least one structural unit has charge-transport properties, i.e. polymers which contain, inter alia, at least one unit selected from groups 1 and 2.

Preferred compounds according to the invention are polymers which simultaneously, besides structural units of the formula (I), additionally contain one or more units selected from groups 1 to 8. It may furthermore be preferred for more than one structural unit from one group to be present simultaneously.

It is likewise preferred for the polymers according to the invention to contain units which improve the charge transport and/or charge injection, i.e. units from group 1 and/or 2; a proportion of 0.5 to 50 mol % of these units is particularly preferred; a proportion of 1 to 30 mol % of these units is very particularly preferred.

It is furthermore particularly preferred for the polymers according to the invention to contain structural units from group 7 and units from group 1 and/or 2. It is particularly preferred for the sum of structural units of the formula (I), of units of group 7 and units from group 1 and/or 2 of the polymer to be at least 50 mol %, based on all units of the polymer, where 0.5 to 50 mol % of units are preferably from group 1 and/or 2.

The way in which the above-mentioned copolymers can be obtained and which further structural elements are particularly preferred for this purpose is described in detail, for example, in WO 2005/014688 A2. This becomes part of the disclosure content of the present application by way of reference. It should likewise be emphasised at this point that the polymer may also have dendritic structures.

The synthesis of the above-described units from groups 1 to 8 and of the further emitting units is known to the person skilled in the art and is described in the literature, for example in WO 2005/014689 A2, in WO 2005/030827 A1 and in WO 2005/030828 A1. These documents and the literature cited therein are part of the technical teaching disclosed in the present application by way of reference.

For the synthesis of the compounds according to the invention, a polymerisation reaction with one or more different monomer building blocks is generally carried out, where at least one monomer incorporated into the polymer results in structural units of the formula (I). Suitable polymerisation reactions are known to the person skilled in the art and are described in the literature. Particularly suitable and preferred polymerisation reactions which result in C—C or C—N links are the following: SUZUKI, YAMAMOTO, STILLE, HECK, NEGISHI, SONOGASHIRA, HIYAMA, ULLMANN, WITTIG or HARTWIG-BUCHWALD polymerisation. The way in which the polymerisation can be carried out by these methods and the way in which the polymers can then be separated off from the reaction medium and purified is known to the person skilled in the art and is described in detail in the literature, for example in WO 03/048225 A2, in WO 2004/037887 A2 and in WO 2004/037887 A2.

The present application thus also relates to a process for the preparation of the polymers according to the invention, which is characterised in that they are prepared by SUZUKI, YAMAMOTO, STILLE, HECK, NEGISHI, SONOGASHIRA, HIYAMA, ULLMANN, WITTIG or HARTWIG-BUCHWALD polymerisation.

The dendrimers according to the invention can be prepared by processes known to the person skilled in the art or analogously thereto. Suitable processes are described in the literature, for example in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6, WO 02/067343 A1 and WO 2005/026144 A1.

For the synthesis of the polymers according to the invention, the corresponding monomers of the formula (II) are required.

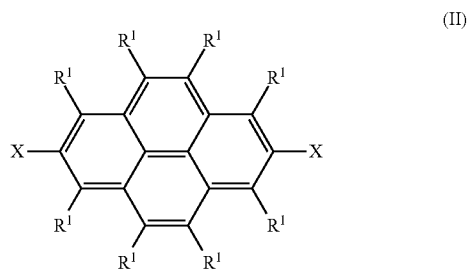

Monomers which result in structural units of the formula (I) in the polymers according to the invention are compounds which are correspondingly substituted and have at two positions suitable functionalities which allow this monomer unit to be incorporated into the polymer. The present application thus likewise relates to these monomers of the formula (II). The symbols $R^1$ used in formula (II) are defined as described in relation to formula (I). The group X represents, identically or differently, a leaving group which is suitable for a polymerisation reaction, so that the incorporation of the monomer building blocks into polymeric compounds is facilitated. X preferably represents a chemical functionality which is selected, identically or differently, from the class of the halogens, O-tosylates, O-triflates, O-sulfonates, boric acid esters, partially fluorinated silyl groups, diazonium groups and organotin compounds.

The basic structure of the monomer compounds can be functionalised by standard methods, for example by Friedel-Crafts alkylation or acylation. Furthermore, the basic structure can be halogenated by standard methods of organic chemistry. The halogenated compounds can optionally be reacted further in additional functionalisation steps. For example, the halogenated compounds can be employed, either directly or after conversion into a boronic acid derivative or organotin derivative, as starting materials for the reaction to give polymers, oligomers or dendrimers.

The said methods merely represent a selection from the reactions known to the person skilled in the art which the latter will be able to employ, without being inventive, for the synthesis of the compounds according to the invention.

It may be preferred to use the polymers according to the invention not as pure substance, but instead as a mixture (blend) together with further polymeric, oligomeric, dendritic or low-molecular-weight substances of any desired type. These may, for example, improve the electronic properties or emit themselves. Mixture above and below is taken to mean a composition which comprises at least one polymeric component.

The present application thus furthermore relates to a mixture (blend) which comprises one or more polymers according to the invention, and one or more further polymeric, oligomeric, dendritic or low-molecular-weight substances.

In a further embodiment of the present application, it is preferred for a mixture to comprise a polymer according to the invention containing structural units of the formula (I) and a low-molecular-weight substance.

In a further embodiment according to the invention, it is preferred for a mixture to comprise a polymer according to the invention, an emitter, which is either present in the polymer according to the invention or, as in the above-mentioned embodiments, admixed as low-molecular-weight substance, and further low-molecular-weight substances. These low-molecular-weight substances can have the same functionalities as mentioned for possible monomer building blocks in groups 1 to 8.

The present application furthermore relates to formulations comprising one or more polymers according to the invention and at least one solvent. The way in which solutions of this type can be prepared is known to the person skilled in the art and is described, for example, in WO 02/072714 A1, in WO 03/019694 A2 and in the literature cited therein.

Suitable and preferred solvents are, for example, toluene, anisole, o-, m- or p-xylene, methyl benzoate, mesitylene, tetralin, veratrol, tetrahydrofuran (THF), methyl-THF, tetrahydropyran (THP), chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphtalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

These solutions can be used to produce thin polymer layers, for example by surface-coating methods (for example spin coating) or by printing processes (for example ink-jet printing).

The polymers, mixtures and formulations according to the invention can be used in electronic or opto-electronic devices or for the production thereof.

The present application relates to the use of the polymers, mixtures and formulations according to the invention in electronic or opto-electronic devices, preferably in organic electroluminescent devices (OLED), organic light-emitting electrochemical cells (OLEC), organic field-effect transistors (OFETs), organic integrated circuits (O-ICs), organic thin-film transistors (TFTs), organic solar cells (O-SCs), organic laser diodes (O-lasers), organic photovoltaic elements or devices (OPV) or organic photoreceptors (OPCs), particularly preferably in organic electroluminescent devices (OLED).

The present application is focused on the use of the compounds according to the invention in organic electroluminescent devices (OLEDs). However, it is possible for the person skilled in the art, without further inventive step, also to employ the compounds according to the invention for further uses in other electronic devices.

For the purposes of the present invention, it is preferred for the polymer, oligomer or dendrimer according to the invention to be in the form of a layer (or to be present in a layer) in the electronic device.

The present application thus also relates to a layer, in particular an organic layer, comprising one or more polymers according to the invention.

The compounds are preferably used in organic electronic devices comprising at least one layer comprising one or more of the polymers according to the invention. Preference is given to the use, in particular, in organic electroluminescent devices comprising anode, cathode and at least one emitting layer, characterised in that at least one layer comprises at least one polymer according to the invention which has structural units of the formula (I).

In a further embodiment, it is preferred for the polymer containing structural units of the formula (I) to be employed together with an emitting compound in an emitting layer. The mixture of the polymer containing structural units of the formula (I) and the emitting compound then comprises between 99 and 1% by weight, preferably between 98 and 60% by weight, particularly preferably between 97 and 70% by weight, in particular between 95 and 75% by weight, of the polymer, based on the entire mixture of emitter and matrix material. Correspondingly, the mixture comprises between 1 and 99% by weight, preferably between 2 and 40% by weight, particularly preferably between 3 and 30% by weight, in particular between 5 and 25% by weight, of the emitter, based on the entire mixture of emitter and matrix material.

In still a further embodiment of the present invention, the polymers according to the invention are employed as hole-transport material or as hole-injection material. The polymer is preferably employed in a hole-transport layer or in a hole-injection layer. These hole-injection layers according to the invention are, for example, triarylamines, carbazoles, silanes or phosphines.

A hole-injection layer in the sense of the present application is a layer which is directly adjacent to the anode. A hole-transport layer in the sense of the present application is a layer which is located between a hole-injection layer and an emission layer. If polymers according to the invention are used as hole-transport material or as hole-injection material, it may be preferred for them to be doped with electron-acceptor compounds, for example with $F_4$-tetracyanoquinodimethane (TCNQ) or with compounds as described in EP 1476881 and in EP 1596445.

In addition, the polymers according to the invention can be used in charge-blocking layers. These charge-blocking layers can consist of various suitable materials, including aluminium oxide, polyvinylbutyral, silane and mixtures thereof. This layer, which is generally applied by known coating techniques, can be of any effective thickness, preferably in the range from 0.05 to 0.5 μm.

The present application furthermore relates to electronic or opto-electronic components, preferably organic electroluminescent devices (OLED), organic light-emitting electrochemical cells (OLEC), organic field-effect transistors (OFETs), organic integrated circuits (O-ICs), organic thin-film transistors (TFTs), organic solar cells (O-SCs), organic laser diodes (O-lasers), organic photovoltaic elements or devices (OPV) or organic photoreceptors (OPCs), particularly preferably organic electroluminescent devices having one or more active layers, where at least one of these active layers comprises one or more polymers according to the invention. The active layer can be, for example, a light-emitting layer, a charge-transport layer and/or a charge-injection layer. The way in which OLEDs can be produced is known to the person skilled in the art and is described, for example, as a general process in detail in WO 2004/070772 A2, which should be adapted correspondingly for the individual case.

Preference is given to an organic electroluminescent device, characterised in that one or more layers are produced from solution, such as, for example, by spin coating, or by means of any desired printing process, such as, for example, roll to roll, screen printing, flexographic printing or offset printing, but particularly preferably LITI (light induced thermal imaging, thermal transfer printing), ink-jet printing, dipping processes or spraying processes. Soluble compounds are necessary for this purpose.

Apart from cathode, anode and the emitting layer, the organic electroluminescent device may also comprise further layers. These can be selected, for example, from charge-carrier injection, charge-carrier transport or charge-carrier blocking layer (T. Matsumoto et al., *Multiphoton Organic EL Device Having Charge Generation Layer*, IDMC 2003, Taiwan; Session 21 OLED (5)). However, it should be pointed out that each of these layers does not necessarily have to be present and in addition a plurality of layers having the same function may be present.

In a further preferred embodiment of the present invention, the organic electroluminescent device comprises a plurality of emitting layers, where at least one layer comprises at least one polymer according to the invention. The emission layers preferably have a plurality of emission maxima between 380 nm and 750 nm, resulting overall in this case in white emission. Particular preference is given to three-layer systems, where at least one of these layers comprises at least one polymer according to the invention and where the three layers exhibit blue, green and orange or red emission (for the basic structure see, for example, WO 05/011013).

The present application thus relates both to the devices themselves and also to the use of the polymers according to the invention in the corresponding devices.

All preferred and not explicitly preferred features of the above-mentioned polymers according to the invention, the use thereof in electronic devices and the electronic devices themselves can be combined with one another as desired. All resultant combinations are likewise part of the present application.

The compounds according to the invention preferably have one or more of the following advantageous properties on use in organic electroluminescent devices:

1. The polymers according to the invention have a large band gap, so that deeper-blue singlet emission is achieved for display applications having a large colour space. The larger band gaps in the polymers according to the invention additionally enable the use thereof as host materials, not only for red, but also for green triplet emission.
2. The compounds according to the invention increase the lifetime and efficiency, in particular of blue-emitting organic electroluminescent devices for high-value applications.

The following examples are intended to explain the present invention in greater detail without restricting it. In particular, the features, properties and advantages described therein of the defined compounds on which the relevant example is based can also be applied to other compounds which are not mentioned in detail, but fall within the scope of protection of the claims, unless mentioned otherwise elsewhere.

WORKING EXAMPLES

A) Preparation of the Monomers

Example 1

Bis-2,7-(1,3,2-dioxaborolane)pyrene

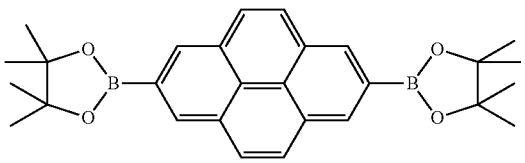

M1

20 g (99 mmol) of pyrene, 55 g (217 mmol) of bisborolane and 400 mg (mmol) of di-tert-butylbipyridine are suspended in 300 ml of cyclohexane and carefully degassed. 500 mg of dimethoxybiscyclooctadienediiridium are added to the reaction mixture, which is then warmed overnight at 80° C. The solution is cooled to room temperature, 100 ml of water and 100 ml of dichloromethane are added. The phases are separated, and the aqueous phase is extracted twice with dichloromethane. The combined organic phases are dried over magnesium sulfate, filtered, and the solvent is stripped off in vacuo. The brown residue is washed a number of times with ethanol, giving 38.9 g (85.6 mmol) (86%) of a white solid having an of purity 99.9%.

Comparative Example 2

Bis-1,6-(1,3,2-dioxaborolan)pyrene

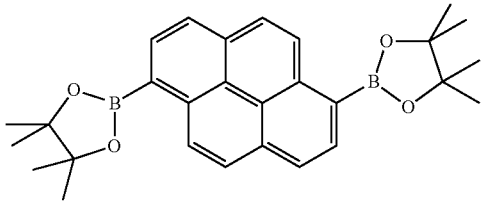

M2

1st Step: Preparation of 1,4- and 1,6-dibromopyrene

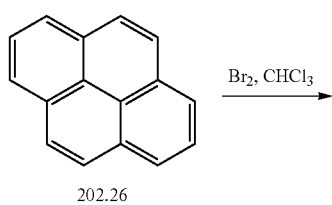

202.26

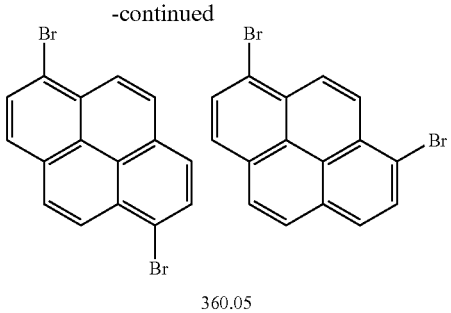

360.05

58 g (288 mmol) of pyrene, dissolved in 1500 ml of dichloromethane, are initially introduced in a 4 l four-necked flask, fitted with reflux condenser, gas outlet into a wash bottle containing NaOH solution, precision-glass stirrer and 500 ml dropping funnel. This solution is heated to the boil. 31.2 ml (600 mmol) of bromine, dissolved in 240 ml of dichloromethane, are added dropwise to this boiling solution over the course of 6 hours (until the formation of gas is complete). The mixture is subsequently boiled under reflux for a further 30 minutes. The solution is then allowed to cool and crystallise overnight. The precipitate is filtered off with suction and washed with ethanol and heptane. The yield is 74.8 g (72%).

The two isomers formed, 1,6 dibromopyrene and 1,8 dibromopyrene, are subjected to fractional sublimation in a carrier-gas sublimation at $10^{-2}$ mbar and 230 to 250° C., the carrier gas used is argon, where the 1,6 dibromopyrene condenses somewhat later and accumulates at the front in the sublimation tube. 24.9 g (33.3%) of a white solid having a purity of 99.9% are obtained.

2nd Step: Conversion of the Bisbromide into the Bisboronic Acid Ester 15 g (41.7 mmol) of dibromopyrene are dissolved in 250 ml of dioxane, and 12.7 g (50 mmol) of bis(pinacolato)diborane and 8 g (81.5 mmol) of potassium acetate are added. 163 mg (0.2 mmol) of 1,1-bis(diphenylphosphino)ferrocenepalladium(II) chloride (complex with dichloromethane (1:1), Pd 13%) is subsequently added, and the batch is warmed to 110° C. After a TLC check, the batch is cooled to room temperature, and 200 ml of water are added. The phases are subsequently separated. The organic phase is washed water, and the aqueous phase is extracted with ethyl acetate, the combined organic phases are then dried over magnesium sulfate, filtered, and the solvent is stripped off in vacuo. The residue is recrystallised from ethanol, giving 17.2 g (37.9 mmol) (91%) of a white solid of purity 99.6%.

B) Preparation of the Polymers

Polymers P1 to P4 according to the invention and comparative polymers V1 to V6 are synthesised by SUZUKI coupling in accordance with WO 03/048225 A2 using the following monomers (percent data=mol %).

The monomers employed, besides the 2,7-pyrenebisboronic ester M1 and the 1,6-pyrenebisboronic ester M2, are the following monomers, whose preparation has already been disclosed in the prior art:

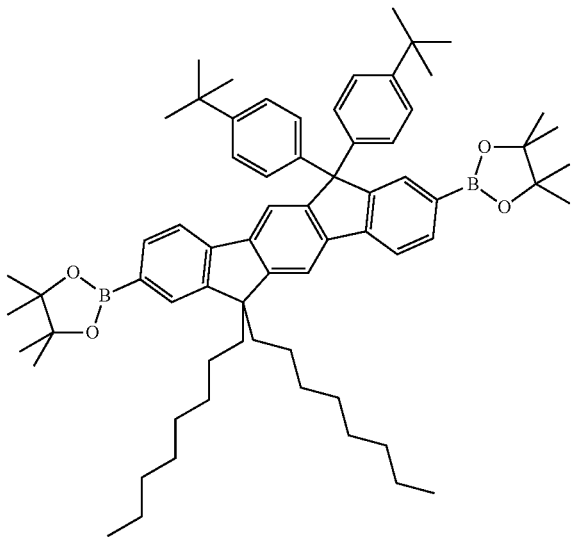

M3

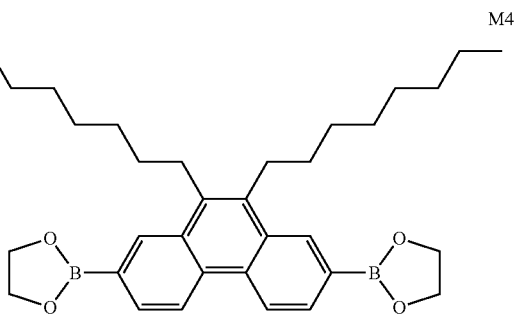

M4

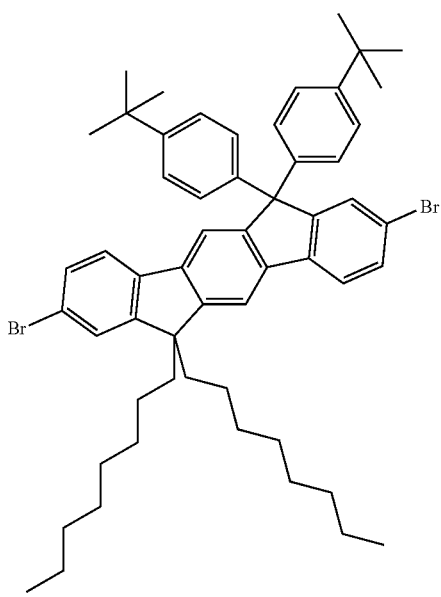

M5

-continued

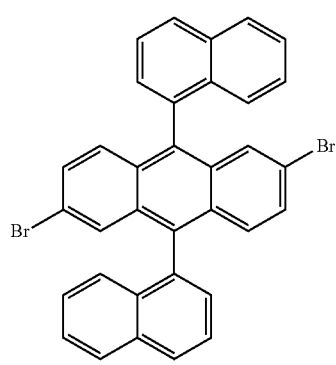
M6

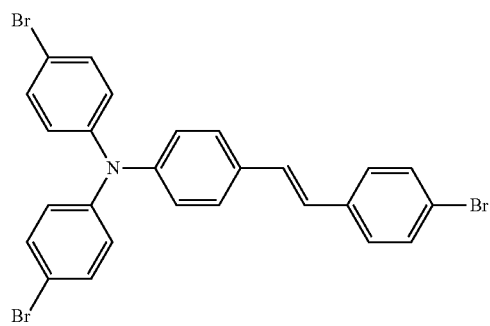
M7

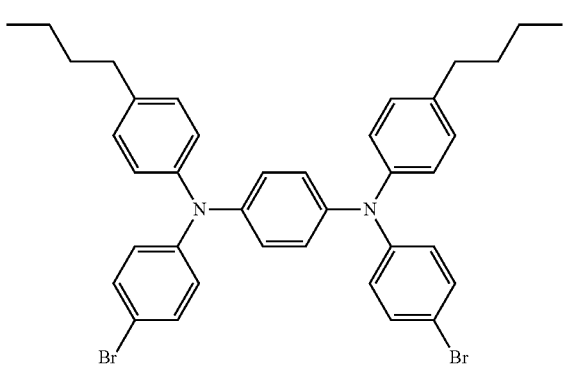
M8

-continued

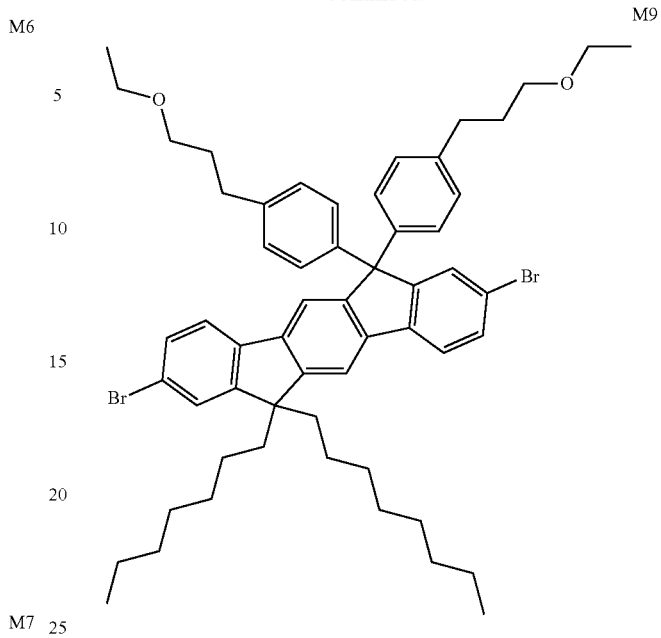
M9

The monomers are copolymerised in the composition shown in Table 1 below, giving polymers P1 to P4 according to the invention and comparative polymers V1 to V6 in the compositions indicated [in mol %], where the sum always corresponds to 100% and bromides and boronic esters are used in equal parts.

TABLE 1

| Polymer | M1 | M2 | M3 | M4 | M5 | M6 | M7 | M8 | M9 |
|---------|----|----|----|----|----|----|----|----|----|
| P1 | 50 | | | | | 2 | | 1.5 | 46.5 |
| V1 | | | | 50 | | 2 | | 1.5 | 46.5 |
| V2 | | | 50 | | | 2 | | 1.5 | 46.5 |
| V3 | | 50 | | | | 2 | | 1.5 | 46.5 |
| P2 | 50 | | | | | | 2 | 1.5 | 46.5 |
| V4 | | | | 50 | | | 2 | 1.5 | 46.5 |
| P3 | 50 | | | | | 7 | | 1.5 | 41.5 |
| V5 | | | | 50 | | 7 | | 1.5 | 41.5 |
| P4 | 50 | | | | | 2.5 | | | 47.5 |
| V6 | | | | 50 | | | | 3 | 47 |

C) Production of the OLEDs

The production of an organic light-emitting diode (OLED) has already been described many times in the literature (for example in WO 2004/037887 A2). In order to explain the present invention by way of example, OLEDs comprising polymers P1 to P4 according to the invention and comparative polymers V1 to V6 from Table 1 (with different proportions of the monomers) are produced by spin coating.

To this end, use is made of substrates from Technoprint (soda-lime glass), to which the ITO structure (indium tin oxide, a transparent, conductive anode) is applied.

The substrates are cleaned with DI water and a detergent (Deconex 15 PF) in a clean room and then activated by UV/ozone plasma treatment. An 80 nm layer of PEDOT (PEDOT is a polythiophene derivative (Baytron P VAI 4083sp.) from H.C. Starck, Goslar, which is supplied as aqueous dispersion) is then applied as buffer layer by spin coating, likewise in the clean room. The spin rate required depends on the degree of dilution and the specific spincoater geometry (typically for 80 nm: 4500 rpm). In order to remove residual water from the layer, the substrates are dried by heating on a hotplate at 180° C. for 10 minutes. Then, under inert-gas atmosphere (nitrogen or argon), firstly 20 nm of an interlayer (typically a hole-dominated polymer, here HIL-012 from Merck) and then 65 nm of the polymer layers are applied from toluene solutions (concentration of interlayer in each case 5 g/l, for polymers P1 to P4 and in each case 8 g/l for comparative polymers V1 to V6). Both layers are dried by heating at 180° C. for at least 10 minutes. The Ba/Al cathode is then applied by vapour deposition (high-purity metals from Aldrich, particularly barium 99.99% (Order No. 474711); vapour-deposition units from Lesker or others, typical vapour-deposition pressure $5 \times 10^{-6}$ mbar). In order to protect, in particular, the cathode against air and atmospheric moisture, the device is finally encapsulated and then characterised.

To this end, the devices are clamped into holders manufactured specifically for the substrate size and provided with spring contacts. A photodiode with eye response filter can be placed directly on the measurement holder in order to exclude influences from extraneous light.

The voltages are typically increased from 0 to max. 20 V in 0.2 V steps and reduced again. For each measurement point, the current through the device and the photocurrent obtained is measured by the photodiode. In this way, the IVL data of the test devices are obtained. Important parameters are the measured maximum efficiency ("eff." in cd/A) and the voltage required for 1000 cd/m².

In order, in addition, to know the colour and the precise electroluminescence spectrum of the test devices, the voltage required for 1000 cd/m² is applied again after the first measurement, and the photodiode is replaced by a spectrum measuring head. This is connected to a spectrometer (Ocean Optics) by an optical fibre. The colour coordinates (CIE: Commission International de l'éclairage, standard observer from 1931) can be derived from the measured spectrum.

The results obtained on use of polymers P1 to P4 according to the invention and comparative polymers V1 to V6 in OLEDs are summarised in Table 2 below.

TABLE 2

| Polymer | CIE [x:y] | U [V] @ 1000 cd/m² | Eff. [cd/A] | LT [hrs] @ 1000 cd/m² | $\lambda_{max}$ [nm] |
| --- | --- | --- | --- | --- | --- |
| P1 | 0.14/0.17 | 6.2 | 5.4 | 2500 | 457 |
| V1 | 0.14/0.19 | 6.3 | 5.4 | 2300 | 463 |
| V2 | 0.14/0.21 | 6.2 | 5.6 | 2100 | 473 |
| V3 | 0.16/0.28 | 6.3 | 5.4 | 1300 | 480 |
| P2 | 0.15/0.17 | 6.3 | 6.4 | 2200 | 459 |
| V4 | 0.15/0.19 | 6.3 | 6.5 | 1900 | 464 |
| P3 | 0.14/0.18 | 6.1 | 5.6 | 1900 | 458 |
| V5 | 0.14/0.20 | 6.2 | 5.7 | 1600 | 464 |
| P4 | NA | NA | NA | NA | NA |
| V6 | NA | NA | NA | NA | NA |
| 80% of P4 + 20% of V6 | 0.14/0.17 | 6.1 | 5.3 | 2100 | 457 |

As can be seen from the results in Table 2, the polymers according to the invention have a deeper-blue emission than comparable polymers of the prior art. Table 2 furthermore shows that polymer blends also exhibit a deep-blue emission, even if only one component, namely the component which comprises the emitter, contains the structural unit of the formula (I) according to the invention.

In addition, the polymers according to the invention result in longer lifetimes.

The invention claimed is:
1. A polymer containing one or more structural units of the formula (Ib) or IIc),

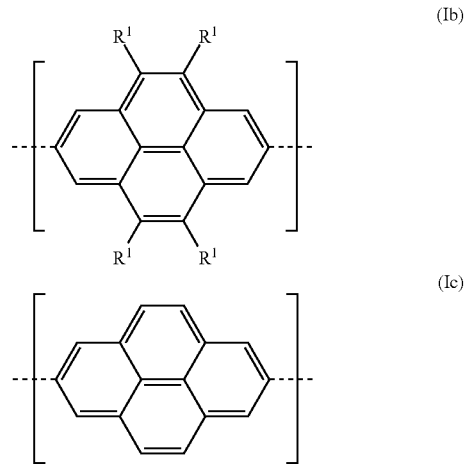

where
$R^1$ on each occurrence, identically or differently, H, D, F, Cl, Br, I, OH, $N(R^2)_2$, a straight-chain alkyl, alkoxy or thioalkoxy group having 1 to 40 C atoms or a branched or cyclic alkyl, alkoxy or thioalkoxy group having 3 to 40 C atoms, in which, in addition, one or more H atoms is optionally replaced by $R^2$ and in which, in addition, one or more non-adjacent $CH_2$ groups is optionally replaced by O, S, $Si(R^2)_2$, $Ge(R^2)_2$, $BR^2$, $NR^2$, $PR^2$, CO, C=S, C=Se, C=$NR^2$, $PO(R^2)$, $PS(R^2)$, $R^2C$=$CR^2$, C≡C, SO, $SO_2$, COO, O(CO)O or $CONR^2$, or a mono- or polycyclic, aromatic or heteroaromatic ring system;
$R^2$ on each occurrence, identically or differently, H, F, a straight-chain alkyl, alkoxy or thioalkoxy group having 1 to 40 C atoms or a branched or cyclic alkyl, alkoxy or thioalkoxy group having 3 to 40 C atoms, in which, in addition, one or more H atoms is optionally replaced by F and in which, in addition, one or more non-adjacent $CH_2$ groups is optionally replaced by O, CO, COO or O(CO)O, or a mono- or polycyclic, aromatic or heteroaromatic ring system; and
the dashed lines represent the bonds to the adjacent structural units
and wherein
(i) the proportion of the structural units of the formula (I) in the polymer is 30 to 60 mol %;
(ii) the polymer contains 0.5 to 50 mol % of units which improve the charge transport and/or charge injection and said units are (iv) units which have hole-injection and/or hole-transport properties and/or (v) units which have electron-injection and/or electron-transport properties; and
(iii) the polymer contains units which are used as a polymer backbone;
wherein
(iv) the units which have hole-injection and/or hole-transport properties are selected from the group consisting of triarylamine, benzidine, tetraaryl-para-phenylenediamine, triarylphosphine, phenothiazine, phenoxazine, dihydrophenazine, thianthrene, dibenzo-para-dioxin, phenoxathiyne, carbazole, azulene, thiophene, pyrrole and furan derivatives;

(v) the units which have electron-injection and/or electron-transport properties are selected from the group consisting of pyridine, pyrimidine, pyridazine, pyrazine, oxadiazole, quinoline, quinoxaline, anthracene, benzanthracene, pyrene, benzimidazole, triazine, ketone, phosphine oxide and phenazine derivatives, and (vi) the units which are used as the polymer backbone are selected from the group consisting of 4,5-dihydropyrene derivatives, 4,5,9,10-tetrahydropyrene derivatives, fluorene derivatives, 9,9'-spirobifluorene derivatives, phenanthrene derivatives, 9,10-dihydrophenanthrene derivatives, 5,7-dihydrodibenzoxepine derivatives and cis- and trans-indenofluorene derivatives.

2. The polymer according to claim 1, wherein the polymer has a molecular weight $M_w$ in the range from 1,000 to 2,000,000 g/mol.

3. A formulation comprising at least one polymer according to claim 1 and at least one solvent.

4. An organic electronic device comprising the formulation according to claim 3.

5. The organic electronic device according to claim 4, having one or more active layers, wherein at least one of the active layers comprises one or more polymers of the formula (1).

6. The organic electronic device according to claim 4, wherein the device is an organic electroluminescent device (OLED), an organic light-emitting electrochemical cell (OLEC), an organic integrated circuit (O-IC), an organic field-effect transistor (OFET), organic thin-film transistor (OTFT), an organic solar cell (O-SC), an organic laser diode (O-laser), an organic photovoltaic element or a corresponding device (OPV) or an organic photoreceptor (OPC).

7. The organic electronic device according to claim 6, wherein the device is an OLED.

8. An organic electronic device comprising the polymer according to claim 1.

9. The organic electronic device according to claim 8, wherein the device is an organic electroluminescent device (OLED), an organic light-emitting electrochemical cell (OLEC), an organic integrated circuit (O-IC), an organic field-effect transistor (OFET), organic thin-film transistor (OTFT), an organic solar cell (O-SC), an organic laser diode (O-laser), an organic photovoltaic element or a corresponding device (OPV) or an organic photoreceptor (OPC).

10. The organic electronic device according to claim 9, wherein the device is an OLED.

11. An organic electronic device having one or more active layers, wherein at least one of the active layers comprises one or more polymers according to claim 1.

12. The polymer according to claim 1, wherein the polymer contains units which have hole-injection and/or hole-transport properties.

13. The polymer according to claim 1, wherein the polymer contains units which have electron-injection and/or electron-transport properties.

14. The polymer according to claim 1, wherein the polymer contains units which have hole-injection and/or hole-transport properties and units which have electron-injection and/or electron-transport properties.

15. The polymer according to claim 1, wherein the units which have hole-injection and/or hole-transport properties are selected from the group consisting of triarylamine, benzidine, tetraaryl-para-phenylenediamine, triarylphosphine, phenothiazine, phenoxazine, dihydrophenazine, thianthrene, dibenzo-para-dioxin, phenoxathiyne, carbazole, azulene, thiophene, and furan derivatives.

* * * * *